US009296718B2

(12) United States Patent
Noti et al.

(10) Patent No.: US 9,296,718 B2
(45) Date of Patent: *Mar. 29, 2016

(54) PREPARATION OF 3,5-DIOXO HEXANOATE ESTER IN TWO STEPS

(71) Applicant: Lonza Ltd, Visp (CH)

(72) Inventors: Christian Noti, Brig-Glis (CH); Guixian Hu, Visp (CH); Barry Jackson, Brig-Glis (CH)

(73) Assignee: Lonza Ltd, Visp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,682

(22) Filed: Aug. 28, 2014

(65) Prior Publication Data

US 2014/0371451 A1    Dec. 18, 2014

Related U.S. Application Data

(62) Division of application No. 14/008,634, filed as application No. PCT/EP2012/055581 on Mar. 29, 2012, now Pat. No. 8,859,786.

(60) Provisional application No. 61/526,321, filed on Aug. 23, 2011, provisional application No. 61/526,307, filed on Aug. 23, 2011, provisional application No. 61/472,820, filed on Apr. 7, 2011, provisional application No. 61/470,548, filed on Apr. 1, 2011.

(30) Foreign Application Priority Data

| Apr. 1, 2011 | (EP) | 11002723 |
| Apr. 7, 2011 | (EP) | 11002922 |
| Aug. 23, 2011 | (EP) | 11006862 |
| Aug. 23, 2011 | (EP) | 11006872 |
| Sep. 19, 2011 | (EP) | 11007605 |
| Sep. 19, 2011 | (EP) | 11007606 |
| Jan. 12, 2012 | (EP) | 12150867 |
| Jan. 12, 2012 | (EP) | 12150868 |

(51) Int. Cl.
| C07D 319/00 | (2006.01) |
| C07D 319/06 | (2006.01) |
| C07C 67/03 | (2006.01) |
| C07C 67/32 | (2006.01) |
| C07C 67/05 | (2006.01) |
| C07C 67/297 | (2006.01) |
| C07D 207/34 | (2006.01) |
| C07D 239/42 | (2006.01) |

(52) U.S. Cl.
CPC .............. *C07D 319/06* (2013.01); *C07C 67/03* (2013.01); *C07C 67/05* (2013.01); *C07C 67/297* (2013.01); *C07C 67/32* (2013.01); *C07D 207/34* (2013.01); *C07D 239/42* (2013.01)

(58) Field of Classification Search
CPC ...................................... C07D 319/00
USPC ............................................. 549/274
See application file for complete search history.

(56) References Cited

U.S. PATENT DOCUMENTS

| 3,666,793 | A | 5/1972 | Stocker et al. |
| 4,970,313 | A | 11/1990 | Wess et al. |
| 8,859,786 | B2 * | 10/2014 | Noti et al. ............ 549/274 |
| 2005/0124639 | A1 | 6/2005 | Joshi et al. |

FOREIGN PATENT DOCUMENTS

| EP | 0037015 | 10/1981 |
| EP | 1 024 139 A1 | 8/2000 |
| EP | 1 609 793 A1 | 12/2005 |
| WO | WO 01/72706 A1 | 10/2001 |
| WO | WO 03/072793 | 9/2003 |

OTHER PUBLICATIONS

Dorwald F. A. Side Reactions in Organic Synthesis, 2005, Wiley: VCH, Weinheim pg. IX of Preface p. 1-15.*
Opinion of International Searching Authority for PCT/EP2012/055581, dated Mar. 2013.
Opinion of the International Preliminary Examining Authority for PCT/EP2012055581, dated Mar. 2013.
International Preliminary Report on Patentability for PCT/EP2012/055581, dated Jul. 2013.
EP Search Report for EP11002922, dated May 2011.
International Search Report for PCT/EP2012/055581; dated May 14, 2012.
Wolberg, et al., "Biocatalytic Reduction of β,δ-Diketo Ester: A Highly Stereoselective Approach to All Four Stereoisomers of a Chlorinatedβ,δ-Dihydroxy Hexanoate:"; Chem. Eur. J. 8, No. 21, 2001, 4561-4571.
Lokot, et al.; "A New Approach to the Synthesis of 3,6- and 5,6-Dialkyl Derivatives of 4-Hydroxy-2-pyrone, Synthesis of rac-Germicidin"; Institute of Bioorganic Chemistry Academy of Sciences of Belarus, 1999, 4783-4792.
Brower, et al., "The Synthesis of (4R-cis)-1,1-Dimethylethyl 6-cyanomethyl-2,2-dimethyl-1,3-dioxane-4-acetate," Tetrahedron Letters, vol. 33, No. 17, 1992, 2279-2282.
Dorwald, F.A., Side Reactions in Organic Synthesis, 2005, Wiley: VCH, Weinheim p. IX of Preface p. 1-15.
Hase et al., Synthetic Communications, 1980, 10(3), 221-224.
Choi et al., Efficient Synthesis of (3R,5S)-3,5,6-Trihydroxyhexanoic Acid Derivative as a Chiral Side Chain of Statins, Synlett 2008, No. 10, pp, 1523-1525.

* cited by examiner

*Primary Examiner* — Nizal Chandrakumar
(74) *Attorney, Agent, or Firm* — Dority & Manning, P.A.

(57) ABSTRACT

The invention discloses a method for the preparation of tert-butyl 6-chloro-3,5-dioxohexanoate from Meldrum's acid derivative and its use for the preparation of tert-butyl (4R,6S)-(6-hydroxymethyl-2,2-dimethyl-1,3-dioxan-4-yl)acetate (BHA), Rosuvastatin and Atorvastatin.

20 Claims, No Drawings

PREPARATION OF 3,5-DIOXO HEXANOATE ESTER IN TWO STEPS

RELATED APPLICATIONS

The present application is a divisional application of U.S. patent application Ser. No. 14/008,634, filed on Sep. 30, 2013, and claims priority to PCT International Patent Application No. PCT1EP20121055581 having a filing date of Mar. 29, 2012, which claims filing benefit of European Patent Application 12150868.3, having a filing date of Jan. 12, 2012; European Patent Application 12150867.5 having a filing date of Jan. 12, 2012; European Patent Application 11007606.4, having a filing date of Sep. 19, 2011; European Patent Application 11007605.6, having a filing date of Sep. 19, 2011; European Patent Application 11006862.4, having a filing date of Aug. 23, 2011; U.S. Patent Application 61/526,321, having a filing date of Aug. 23, 2011; European Patent Application 11006872.3, having a filing date of Aug. 23, 2011; U.S. Patent Application 61/526,307, having a filing date of Aug. 23, 2011; European Patent Application 11002922.0, having a filing date of Apr. 7, 2011; U.S. Patent Application 61/472,820, having a filing date of Apr. 7, 2011; U.S. Patent Application 61/470,548, having a filing date of Apr. 1, 2011; and European Patent Application 11002723.2, having a filing date of Apr. 1, 2011, all of which are incorporated herein by reference in their entirety.

The invention discloses a method for the preparation of tert-butyl 6-chloro-3,5-dioxohexanoate from Meldrum's acid derivative and its use for the preparation of tert-butyl (4R,6S)-(6-hydroxymethyl-2,2-dimethyl-1,3-dioxan-4-yl)acetate (BHA), Rosuvastatin and Atorvastatin.

BHA is an intermediate in the preparation of Rosuvastatin and Atorvastatin, which are active pharmaceutical ingredients used in respective drugs to treat high cholesterol and related conditions, and to prevent cardiovascular disease. BHA is prepared from a 3,5-dioxo hexanoate ester.

EP 1024139 B discloses a method for preparation of BHA comprising a reaction of an acetate ester with a hydroxybutyric acid derivative to get the intermediate 3,5-dioxo hexanoate ester.

Tetrahedron 55 (1999) 4783-4792 discloses the synthesis of 3,6- and 5,6-dialkyl-4-hydroxy-2-pyrones with the help of Meldrum's acid.

WO 01/72706 A discloses a multistep method for the preparation of BHA and implicitly discloses a precursor, which is the condensation product of a beta-keto butyric acid derivative with meldrum's acid; the hydrolysis thereof provides the respective 3,5-dioxohexanoic acid derivative, the precursor of BHA. The advantages of the instant invention compared to the process disclosed in WO 01/72706 A are discussed below.

The known processes for the preparation of the intermediate 3,5-dioxo hexanoate ester which is used in the preparation of BHA are multi step procedures involving metal containing bases. e.g. derived from lithium or magnesium. There was a need for a simplified process for the preparation of the intermediate 3,5-dioxo hexanoate ester, which necessitates less steps, no use of metal containing bases derived from magnesium or lithium, and provides for higher yields and purer products, which can be isolated in an uncomplicated way. Surprisingly, using a Meldrum's acid intermediate, an efficient method was found.

The following abbreviations are used, if not otherwise stated:

In the following text, halogen means F, Cl, Br or I, preferably Cl, Br or I; more preferably Cl or Br; alkyl means linear and branched alkyl; unless otherwise specified.

Subject of the invention is a method (B) for the preparation of a compound of formula (II);

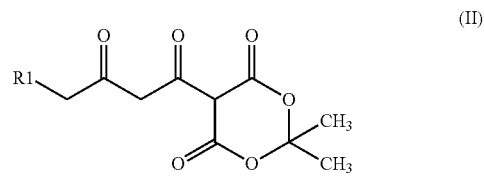

(II)

R1 is Cl, Br and CN;
method (B) comprises a step (C) and a step (B);
step (B) is done after step (C);
step (C) comprises a reaction (C) of a compound of formula (VI) with a compound (C) to provide a compound of formula (IV);

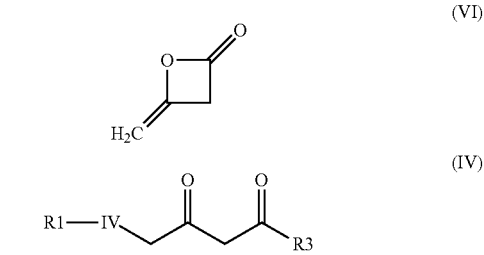

the compound (C) is selected from the group consisting of $Cl_2$, $Br_2$ and ClBr;
step (B) comprises a reaction (B) of the compound of formula (IV), which has been prepared in step (C), with a compound of formula (V) in the presence of a base (B);

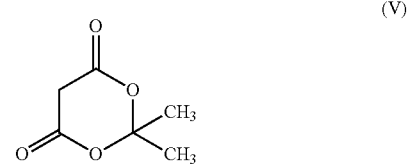

(V)

R1-IV and R3 are identical or different and independently from each other Cl or Br;
base (B) is selected from the group consisting of N(R4)(R5)R6, 1,4-diazabicyclo[2.2.2]octane, a hexamethyldisilazide, a $C_{1-4}$ alkoxide salt of, a $C_{1-10}$ carboxylate salt of, a carbonate salt of, a hydrogen carbonate salt of, a phosphate salt of, a monohydrogenphosphate salt of or a dihydrogenphosphate salt of Na, of K or of Li, 1,8-diazabicyclo[5.4.0]undec-7-ene, $NaNH_2$, $KNH_2$, NaH, KH, $CaH_2$, pyridine, pyridine substituted with 1 or 2 identical or different substituents independently from each other selected from the group consisting of methyl, ethyl and N(R14)R15; morpholine, methylmorpholine, methylpiperidine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, CsCO₃, NaOH, KOH, Ca(OH)₂, n-butyl lithium (BuLi), sec-butyl lithium, tert-butyl lithium, hexyl lithium, methyl lithium and mixtures thereof;

R4, R5, R6 are identical or different and independently from each other selected from the group consisting of H, $C_{1-15}$ alkyl, $C_{5-6}$ cycloalkyl, $(C(R16)R17)_mN(R12)R13$ and phenyl, with the proviso, that at least one of the residues R4, R5 or R6 is not H;

R12 and R13 are identical or different and independently from each other H or $C_{1-15}$ alkyl;

m is 2, 3, 4, 5 or 6;

R14 and R15 are identical or different and independently from each other methyl or ethyl;

R16 and R17 are identical or different and independently from each other selected from the group consisting of H, methyl and ethyl;

with the proviso, that if R1 in formula (II) is CN, then step (B) comprises additionally a reaction (B-add), the reaction (B-add) is done after the reaction (B), of the reaction product of the reaction (B) with a compound (B);

compound (B) is selected from the group consisting of NaCN, KCN, Si(R9)(R10)(R11)CN, HCN, tetrabutylammonium cyanide, 1-cyano benzotriazole and triselenium dicyanide and mixtures thereof;

R9, R10 and R11 are identical or different and independently from each other selected from the group consisting of $C_{1-4}$ alkyl and phenyl.

Formula (IV) comprises all possible tautomeric forms of compound of formula (IV).

Formula (V) comprises all possible tautomeric forms of compound of formula (V).

Base (B), compound of formula (IV) and compound of formula (V) can be added in any sequence.

Preferably, base (B) is used to deprotonate the $CH_2$ moiety of the compound of formula (V).

Preferably, deprotonated compound of formula (V) is added to compound of formula (IV) or vice versa.

The reaction product of the reaction (B), which is reacted with a compound (B) in the reaction (B-add) of step (B) after the reaction (B), is a compound of formula (II-R1-IV);

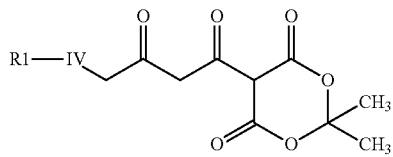

(II-R1-IV)

wherein R1-IV is defined as above, also with all its preferred embodiments.

Formula (II-R1-IV) comprises all possible tautomeric forms of compound of formula (II-R1-IV).

Compounds of formulae (IV) and (V) are known compounds and can be prepared by known methods.

Preferably, R1-IV and R3 are identical and are Cl or Br.

Preferably, R1-IV and R3 are Cl.

Preferably, R4, R5, R6 are identical or different and independently from each other selected from the group consisting of cyclohexyl, phenyl, methyl, ethyl, n-propyl, iso-propyl, n-butyl, iso-butyl, sec-butyl, tert-butyl and $(CH_2)_mN(R12)R13$;

R12 and R13 are identical or different and independently from each other selected from the group consisting of H, methyl, ethyl, n-propyl, iso-propyl, n-butyl, iso-butyl, sec-butyl and tert-butyl;

m is 2, 3 or 4;

R14 and R15 are methyl.

More preferably, R4, R5, R6 are identical or different and independently from each other selected from the group consisting of cyclohexyl, phenyl, methyl, ethyl, n-propyl, iso-propyl and $(CH_2)_mN(R12)R13$;

R12 and R13 are identical or different and independently from each other selected from the group consisting of H, methyl, ethyl, n-propyl and iso-propyl;

m is 2, 3 or 4;

R14 and R15 are methyl.

Even more preferably, R4, R5, R6 are selected from the group consisting of cyclohexyl, phenyl, methyl, ethyl, n-propyl, iso-propyl and $(CH_2)_mN(R12)R13$;

R12 and R13 are selected from the group consisting of H, methyl, ethyl, n-propyl and iso-propyl;

m is 2;

R14 and R15 are methyl.

Especially, R4, R5, R6 are methyl or ethyl and $(CH_2)_mN(R12)R13$;

R12 and R13 are H, methyl or ethyl;

m is 2;

R14 and R15 are methyl.

Base (B) must have the capability to deprotonate the $CH_2$ moiety of the compound of formula (V). Preferably, the pKa value of the corresponding protonated form of base (B) is from 5 to 40, more preferably from 6 to 18, even more preferably from 6 to 13.

Preferably, base (B) is selected from the group consisting of N(R4)(R5)R6, 1,4-diazabicyclo[2.2.2]octane, a hexamethyldisilazide, a $C_{1-4}$ alkoxide salt of, a $C_{1-10}$ carboxylate salt of, a carbonate salt of, a hydrogen carbonate salt of, a phosphate salt of, a monohydrogenphosphate salt of or a dihydrogenphosphate salt of Na, of K or of Li, 1,8-diazabicyclo[5.4.0]undec-7-ene, NaNH₂, KNH₂, NaH, KH, CaH₂, pyridine, pyridine substituted with 1 or 2 independently selected identical or different $C_{1-2}$ alkyl residues, N,N-dimethyl-4-pyridinamine, morpholine, 4-methylmorpholine, 1-methylpiperidine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, CsCO₃, NaOH, KOH, Ca(OH)₂ and mixtures thereof;

with R4, R5 and R6 as defined herein, also with all their preferred embodiments.

More preferably, base (B) is selected from the group consisting of N(R4)(R5)R6, 1,4-diazabicyclo[2.2.2]octane, a hexamethyldisilazide, a $C_{1-4}$ alkoxide salt of, a $C_{1-10}$ carboxylate salt of, a carbonate salt of, a hydrogen carbonate salt of, a phosphate salt of, a monohydrogenphosphate salt of or a dihydrogenphosphate salt of Na, of K or of Li, 1,8-diazabicyclo[5.4.0]undec-7-ene, pyridine, pyridine substituted with 1 or 2 independently selected identical or different $C_{1-2}$ alkyl residues, N,N-dimethyl-4-pyridinamine, morpholine, 4-methylmorpholine, 1-methylpiperidine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, NaOH, KOH, Ca(OH)₂ and mixtures thereof;

R4, R5, R6 are methyl or ethyl and $(CH_2)_mN(R12)R13$;

R12 and R13 are H, methyl or ethyl;

m is 2;

R14 and R15 are methyl.

Even more preferably, base (B) is selected from the group consisting of N(R4)(R5)R6, 1,4-diazabicyclo[2.2.2]octane, a hexamethyldisilazide, a $C_{1-4}$ alkoxide salt of, a $C_{1-10}$ carboxylate salt of, a carbonate salt of, a hydrogen carbonate salt of, a phosphate salt of, a monohydrogenphosphate salt of or a dihydrogenphosphate salt of Na, of K or of Li, 1,8-diazabicyclo[5.4.0]undec-7-ene, pyridine, pyridine substituted with 1 or 2 independently selected identical or different $C_{1-2}$ alkyl residues, N,N-dimethyl-4-pyridinamine, morpholine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, NaOH, KOH, $Ca(OH)_2$ and mixtures thereof;

R4, R5, R6 are methyl or ethyl and $(CH_2)_m N(R12)R13$;

R12 and R13 are H, methyl or ethyl;

m is 2;

R14 and R15 are methyl.

Especially, the base (B) is selected from the group consisting of $NEt_3$, tetramethylethylendiamine and N,N-dimethyl-4-pyridinamine and mixtures thereof.

Preferably, R9, R10 and R11 are identical and are selected from the group consisting of $C_{1-4}$ alkyl.

More preferably, R9, R10 and R11 are methyl.

Also other CN sources, which act as equivalents to those listed for compound (B), can be used.

Preferably, compound (B) is NaCN or KCN.

Reaction (B) can be done in a solvent (B). Preferably, the solvent (B) is selected from the group consisting of hexanes, heptanes, dichloromethane, dichloroethane, chloroform, carbon tetrachloride, toluene, xylene, mesitylene, dioxane, methyl tert-butyl ether and mixtures thereof.

Preferably, the solvent (B) is dichloromethane.

Preferably, the reaction temperature of reaction (B) is from −78 to 100° C., more preferably from −50 to 50° C., even more preferably from −25 to 25° C., especially from −15 to 25° C.

Preferably, the reaction (B) is done at a pressure of from atmospheric pressure to 60 bar, more preferably of from atmospheric pressure to 10 bar, even more preferably of from atmospheric pressure to 2 bar, especially at atmospheric pressure.

Preferably, the reaction time of reaction (B) is from 5 min to 24 h, more preferably from 5 min to 12 h, even more preferably from 1 h to 5 h, especially from 2 h to 3 h.

Preferably, the amount of compound of formula (V) is from 0.5 to 10 mol equivalent, more preferably from 0.9 to 5 mol equivalent, even more preferably from 0.95 to 1.25 mol equivalent, especially from 0.98 to 1.05 mol equivalent, of the mol of compound of formula (IV).

Preferably, the amount of solvent (B) is from 1 to 100 fold, more preferably from 5 to 50 fold, even more preferably from 5 to 20 fold, especially from 5 to 15 fold, of the weight of compound of formula (IV).

Preferably, the molar amount of base (B) is from 0.5 to 10 fold, more preferably from 0.95 to 3 fold, of the molar amount of compound of formula (V).

Preferably, the reaction (B) is done under inert atmosphere.

After the reaction (B), the compound of formula (II) can be isolated from the reaction mixture resulting from reaction (B) by standard methods known to the skilled person such as acidification, filtration, evaporation of volatile components, extraction, washing, drying, concentration, crystallization, distillation and any combination thereof.

Optionally, any organic phase can be dried, preferably with magnesium sulphate or sodium sulphate.

Optionally, compound of formula (II) can be separated from the reaction mixture by addition of an acid (B).

Therefore further subject of the invention is a method (B), which comprises further a step (ACID);

step (ACID) is done after step (B);

step (ACID) comprises combining the reaction mixture prepared in step (B) with an acid (B).

In step (ACID) the reaction mixture prepared in step (B) can be added to acid (B) or vice versa.

Acid (B) is selected from the group consisting of polymeric sulfonic acid resin, toluene sulfonic acid, HCl, $H_2SO_4$, citric acid, tartaric acid, acetic acid, ammonium chloride, oxalic acid, phosphoric acid and mixtures thereof, preferably acid (B) is a polymeric sulfonic acid resin.

Preferably, acid (B) is used without water or at least as a mixture with only a small amount of water, when acid (B) is added to the reaction mixture of step (B), e.g. as gas in case of HCl, without crystal water in the case of e.g. citric or tartaric acid, or as conc. $H_2SO_4$ in case of sulphuric acid.

The water content of acid (B) in this case is preferably 0 to 5% by weight, more preferably 0 to 2.5% by weight, even more preferably 0 to 2% by weight, the % by weight being based on the total weight of acid (B).

When the reaction mixture of step (B) is added to acid (B), then acid (B) is preferably used as a mixture with water, and the water content of acid (B) is preferably 0.5 to 99% by weight.

Preferably, no water is added in step (B). When no water is added in step (ACID), then water or a mixture of acid (B) with water can be added after step (ACID).

Preferably, the amount of acid (B) is 0.5 to 10, more preferably 1 to 3, even more preferably 1.2 to 2 mol equivalents in case when acid (B) is not a polymeric sulfonic acid resin, whereas in case when acid (B) is a polymeric sulfonic acid resin, then acid (B) is used in an amount of 0.5 to 10, more preferably 1 to 5, even more preferably 1.3 to 2 mol equivalents of sulfonic acid groups of acid (B), the mol equivalents being based on the molar amount of base (B).

Preferably, acid (B) is added in such an amount, that the pH is adjusted to 0 to 7, more preferably 0.5 to 7, even more preferably 1 to 7, especially 1 to 4, more especially 1 to 2.

The polymeric sulfonic acid resin is preferably an acidic cation exchange resin, more preferably a strongly acidic cation exchange resin, for example such as used in heterogeneous acid catalysis.

Preferably, the polymeric sulfonic acid resin has an average molecular weight of from 1000 to 1000000 D; and/or preferably a concentration of acid sites of from 1 to 15, more preferably of from 1 to 11.6, even more preferably of from 1 to 10, especially of from 1 to 8, more especially of from 1 to 7 equivalents per kg resin; and/or preferably an acid number of from 1 to 650, more preferably of from 1 to 560, even more preferably of from 1 to 450, especially of from 1 to 350, more especially of from 50 to 650, even more especially of from 1 to 560, in particular of from 50 to 450, more in particular of from 50 to 350; and/or preferably a particle size of from 4 to 800 mesh, more preferably 4 to 400 mesh.

The concentration of acid sites is determined by the Master Test Method MTM 0232, Edition 1.4, © Rohm and Haas Company, 1998, wherein the CATALYST VOLATILES are determined by the Master Test Method MTM 0126, Edition 1.6, © Rohm and Haas Company, 2000.

The acid number is determined according to DIN EN ISO 3682. For further explanation of the acid number and for its relation to the concentration of acid sites see "BASF Handbuch Lackiertechnik", Artur Goldschmidt and Hans-Joachim Streitberger, Vincentz Verlag, 2002, ISBN 3-87870-324-4, chapter 2.3.2.2 (pages 272 to 273). According to the teaching therein, an concentration of acid sites of 1 equivalents per kg equals an acid number of 56, therefore a concentration of acid sites of 4.7 equivalents per kg equals an acid number of 263.

Especially, the polymeric sulfonic acid resin is selected from the group consisting of sulfonated polystyrene resins, sulfonated polystyrene resins crosslinked with divinyl benzene and poly(2-acrylamido-2-methyl-1-propanesulfonic acid).

Sulfonated polystyrene resins crosslinked with divinyl benzene are also called divinylbenzene-styrenesulfonic acid copolymer.

One example for a polymeric sulfonic acid resin is Amberlyst® 15 DRY.

After addition of acid (B) the mixture can be filtered,

Preferably, any volatile components of the reaction mixture are removed by evaporation under reduced pressure.

Any concentration is preferably done by distillation, preferably under reduced pressure.

Even more preferably, the reaction mixture is acidified, the organic phase is separated and concentrated.

Especially, acid (B) is a polymeric sulfonic acid resin and solvent (B) is chosen in such a way, that acid (B) is insoluble in solvent (B). Thereby after acidification by addition of the polymeric sulfonic acid resin the reaction mixture can be filtered, thereby filtering off the resin, and the compound is isolated by evaporation of solvent (B). Thereby no water needs to be added.

The compound of formula (II) can be purified by standard methods known to the skilled person, preferably by crystallization or distillation under reduced pressure.

Compound of formula (VI) is a known compound and can be prepared by known methods.

Preferably, compound (C) is $Cl_2$ or $Br_2$, more preferably $Cl_2$.

Even more preferably, compound (C) is $Cl_2$, R1-IV and R3 are Cl and R1 is Cl or CN.

Reaction (C) can be done in a solvent (C). Preferably, the solvent (C) is selected from the group consisting of hexane, heptane, dichloromethane, dichloroethane, chloroform, carbon tetrachloride, toluene, xylene, mesitylene, dioxane, methyl tert-butyl ether and mixtures thereof.

Preferably, the solvent (C) is dichloromethane.

Preferably, the reaction temperature of reaction (C) is from −78 to 100° C., more preferably from −40 to 40° C., even more preferably from −25 to 25° C., especially from −20 to 20° C.

Preferably, the reaction (C) is done at a pressure of from atmospheric pressure to 60 bar, more preferably of from atmospheric pressure to 10 bar, even more preferably of from atmospheric pressure to 2 bar, especially at atmospheric pressure.

Preferably, the reaction time of reaction (C) is from 1 min to 24 h, more preferably from 1 min to 12 h, even more preferably from 1 min to 6 h, especially from 10 min to 2 h.

Preferably, the amount of compound (C) is from 0.9 to 10 mol equivalent, more preferably from 0.95 to 2 mol equivalent, even more preferably from 0.98 to 1.05 mol equivalent, of the mol of compound of formula (VI).

Preferably, the amount of solvent (C) is from 1 to 100 fold, more preferably from 5 to 50 fold, even more preferably from 5 to 20 fold, especially from 5 to 15 fold, of the weight of compound of formula (VI).

Preferably, the reaction (C) is done under inert atmosphere.

After the reaction (C), the compound of formula (IV) can be isolated from the reaction mixture resulting from reaction (C) by standard methods known to the skilled person such as acidification, filtration, evaporation of volatile components, extraction, washing, drying, concentration, crystallization, distillation and any combination thereof.

Compound of formula (IV) can also be not isolated, but used directly for the next reaction without isolation.

Optionally, any organic phase can be dried, preferably with magnesium sulphate or sodium sulphate.

Preferably, method (B) comprises further a step (A), with method (B) as defined herein, also with all its preferred embodiments;

step (A) is done after step (B);

step (A) comprises a reaction (A) of compound of formula (II), which has been prepared in step (B), with a compound of formula (III) to provide compound of formula (I);

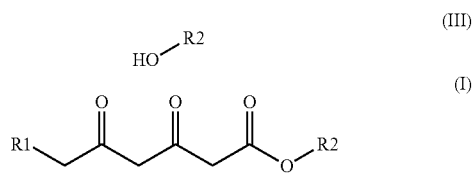

R2 is $C_{1-4}$ alkyl.

Formula (I) comprises all possible tautomeric forms of compound of formula (I).

Formula (II) comprises all possible tautomeric forms of compound of formula (II).

Possible tautomers of compound of formulae (I) are inter alia compound of formula (I-a), compound of formula (I-b) and compound of formula (I-c).

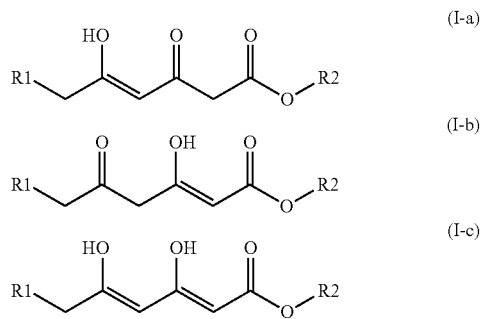

Possible tautomers of compound of formulae (II) are inter alia compound of formula (II-a), compound of formula (II-b) and compound of formula (II-c).

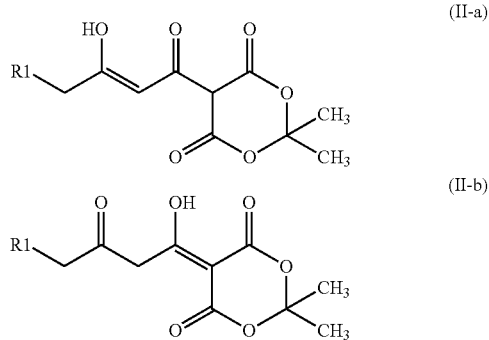

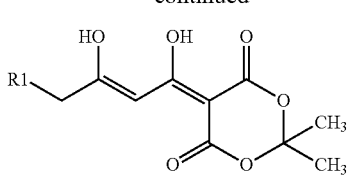

(II-c)

Preferably, R1 is Cl or CN.

More preferably, compound (C) is Cl$_2$, R1-IV and R3 are Cl and R1 is Cl or CN.

Preferably, R2 is selected from the group consisting of methyl, ethyl, n-propyl, iso-propyl, n-butyl, iso-butyl, sec-butyl and tert-butyl;

more preferably, R2 is ethyl or tert-butyl;

even more preferably, R2 is tert-butyl.

Especially, R1 is Cl or CN, and R2 is tert-butyl.

More especially, R1 is Cl or CN, R2 is tert-butyl, compound (C) is Cl$_2$ and R1-IV and R3 are Cl.

Reaction (A) can be done in a solvent (A). Any solvent that does not interfere with the reaction and has a boiling point of preferably 50° C. or more can in principle be used.

Preferably, solvent (A) is selected from the group consisting of hexane, heptane, dichloromethane, dichloroethane, chloroform, toluene, xylene, mesitylene, dioxane, N,N-di-C$_{1-4}$ alkyl C$_{1-4}$ monocarboxamide, di-C$_{1-2}$ alkyl sulfoxide and mixtures thereof.

Preferably, the compound of formula (III) serves also as solvent (A).

Preferably, the compound of formula (III) serves also as solvent (A) and no further solvent (A) is used.

Preferably, the reaction temperature of reaction (A) is from −40 to 180° C., more preferably from 20 to 100° C., even more preferably from 20 to 150° C. especially from 30 to 90° C., more especially from 40 to 85° C.

Preferably, the reaction (A) is done at a pressure of from atmospheric pressure to 60 bar, more preferably of from atmospheric pressure to 10 bar, even more preferably of from atmospheric pressure to 2 bar, especially at atmospheric pressure.

Preferably, the reaction time of reaction (A) is from 5 min to 48 h, more preferably 5 min to 24 h, more preferably from 1 h to 8 h, even more preferably from 1 h to 3 h.

Preferably, the amount of compound of formula (III) is from 1 to 200 mol equivalent, more preferably from 1 to 100 mol equivalent, even more preferably from 1 to 50 mol equivalent, of the mol of compound of formula (II).

Preferably, the amount of solvent (A) is from 0.1 to 100 fold, more preferably from 0.1 to 50 fold, even more preferably from 0.1 to 20 fold, especially from 0.1 to 10 fold, of the weight of compound of formula (II).

Usually, the amount of solvent (A) is at least 2 or 5 fold of the weight of compound of formula (II), therefore further possible ranges are preferably 2 to 100 fold, more preferably from 2 to 50 fold, even more preferably from 2 to 20 fold, especially from 2 to 10 fold, of the weight of compound of formula (II); or preferably 5 to 100 fold, more preferably from 5 to 50 fold, even more preferably from 5 to 20 fold, especially from 5 to 10 fold, of the weight of compound of formula (II).

If compound of formula (III) is not used as solvent, then preferably the amount of compound of formula (II) is from 1 to 2 mol equivalent, more preferably from 1 to 1.5 mol equivalent, even more preferably from 1.1 to 1.5 mol equivalent, of the mol of compound of formula (II).

Reaction (A) can be done in the presence of an acid (A).

Preferably, acid (A) is selected from the group consisting of polymeric sulfonic acid resin, toluene sulfonic acid, HCl, H$_2$SO$_4$, citric acid, tartaric acid, acetic acid, ammonium chloride, oxalic acid, phosphoric acid and mixtures thereof, preferably acid (A) is a HCl.

Preferably, the amount of acid (A) is from 0.1 to 100 fold, more preferably from 0.1 to 50 fold, even more preferably from 0.1 to 20 fold, especially from 0.1 to 10 fold, of the weight of compound of formula (II).

Acid (A) is used without water or as a mixture with water, eg. as aqueous HCl or as aqueous H$_2$SO$_4$ or conc. H$_2$SO$_4$.

The water content of acid (A) is preferably 0 to 99% by weight, the % by weight being based on the total weight of acid (A).

Preferably, the reaction (A) is done under inert atmosphere.

After the reaction (A), the compound of formula (I) can be isolated from the reaction mixture resulting from reaction (A) by standard methods known to the skilled person such as filtration, evaporation of volatile components, extraction, washing, drying, concentration, crystallization, distillation and any combination thereof.

Optionally, colored impurities can be removed by conventionally known treatment with charcoal, eg by treatment with charcoal of the reaction mixture from reaction (B) and/or from reaction (A).

Optionally, any organic phase can be dried, preferably with magnesium sulphate or sodium sulphate.

Preferably, any volatile components of the reaction mixture are removed by evaporation under reduced pressure.

Any concentration is preferably done by distillation, preferably under reduced pressure.

The compound of formula (I) can be purified, preferably by crystallization or distillation under reduced pressure.

Step (ACID) is done after step (B) and before step (A).

Preferably, step (B), optionally step (ACID), and then step (A) are done consecutively without isolating compound of formula (II).

Preferably, an optional solvent (B) and an optional solvent (A) are identical.

More preferably, step (B) and step (A) are done in one pot, and an optional solvent (B) and an optional solvent (A) are identical.

Preferably, step (C) and step (B) are done consecutively without isolating the compound of formula (IV).

Preferably, an optional solvent (C) and an optional solvent (B) are identical.

More preferably, step (C) and step (B) are done in one pot, and an optional solvent (C) and an optional solvent (B) are identical.

Preferably, step (C), step (B) and step (A) are done consecutively without isolating the compounds of formulae (IV) and (II).

Preferably, an optional solvent (C), an optional solvent (B) and an optional solvent (A) are identical.

More preferably, step (C), step (B) and step (A) are done in one pot, and an optional solvent (C), an optional solvent (B) and an optional solvent (A) are identical.

In another preferred embodiment, step (ACID) is done after step (B), compound of formula (II) is isolated, and then step (A) is done and solvent (A) is compound of formula (III); more preferably acid (B) is a polymeric sulfonic acid resin and solvent (B) is chosen in such a way, that acid (B) is insoluble in solvent (B).

Each of the steps (C), (B), (A) and the optional step (ACID) can be done continuously in a flow reactor. Steps (C) and (B), or steps (C), (B), (A) and the optional step (ACID) can also be done consecutively and continuously in a flow reactor without isolation of any intermediate.

Suitable flow reactors are known in the art, there is no specific requirement for a suitable flow reactor to carry out any of the steps (C), (B) or (A) continuously.

Further subject of the invention is a method (PREP) for the preparation of a compound selected from the group consisting of compound of formula (X), compound of formula (XI), compound of formula (XII), Rosuvastatin and Atorvastatin;

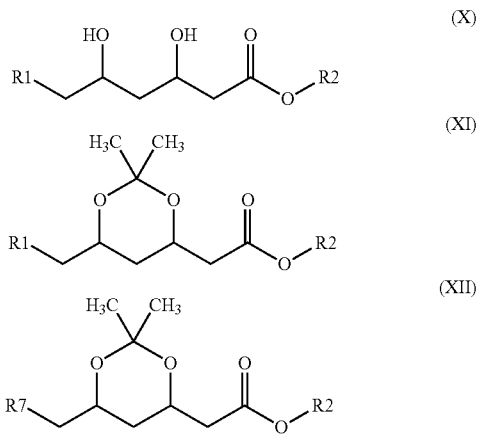

method (PREP) comprises the step (C) and the step (B);
step (C), step (B) and R are as defined herein, also with all their preferred embodiments;
R2 is as defined herein, also with all its preferred embodiments;
R7 is O—C(O)CH$_3$, OH or CH$_2$—NH$_2$.
In one preferred embodiment, method (PREP) comprises also the step (ACID).
In another preferred embodiment, method (PREP) comprises also the step (A).
In another preferred embodiment, method (PREP) comprises also the step (ACID) and the step (A).
Compound of formula (X), compound of formula (XI), compound of formula (XII), compound of formula (XIII), Rosuvastatin and Atorvastatin are known compounds.
The methods for preparation of compound of formula (X), of compound of formula (XI), of compound of formula (XII), of compound of formula (XIII), of Rosuvastatin and of Atorvastatin using compound of formula (II) as intermediate are known.

The method of the present invention does not necessitate mandatorily the use of metal derived bases. It provides the compounds of formulae (I) and (II) in high yields and high purities, the compounds have bright, white color. Compound of formula (II) can be isolated after the reaction in an easy way, especially a mixture of an organic and an aqueous phase separates in the two phases fast and unambiguously, which facilitates isolation considerably. Another easy way to isolate the compounds is the addition of an acid, preferably of an insoluble polymeric sulfonic acid resin, filtration and evaporation of solvent, thereby the use of water can be omitted.

The method is environmentally uncritical; it does not use toxic substances.

Further advantage is the fact, that the disclosed methods can be done at temperature well above −78° C., which are conventionally used in methods, where the C6 scaffold of compound of formula (I) is built up from a reaction of a C4 precursor with an acetic acid ester derivative, for example by aldol condensation and similar reactions.

Further advantages of reaction (A) are the side products: only carbon dioxide and acetone are generated as side products, therefore reaction (A) is an environmentally friendly method. The acetone can even be isolated and used for other purposes.

The WO 01/72706 A discloses in examples 1.4 and 1.5 a process comprising 6 steps, when calculated from the starting C2 building block, which could be applied for the preparation of compound of formula (I), which is the precursor of BHA: 1. Chloroacetic acid is converted to its acid chloride, 2. then reacted with Meldrunm's acid, 3. then converted by hydrolysis to the respective butyric acid derivative, 4. then again converted into the acid chloride, 5. reacted a second time with Meldrum's acid and 6. finally converted by esterfication into the respective derivative of compound of formula (I). Two equivalents each of Meldrum's acid, chlorine, base and alcohol is needed.

The process of the instant invention allows for the preparation of compound of formula (I), which is the precursor of BHA in a 4 step process: 1. acetic acid is converted into diketene, 2. diketene is converted with Cl$_2$ into the chlorinated butyric acid chloride derivative, 3. then reacted with Meldrum's acid, and 4. finally converted by esterfication into compound of formula (I). Only one equivalent Meldrum's acid, chlorine, base and alcohol are needed. Furthermore, no magnesium or lithium derived bases are necessary as is the case in the WO 01/72706 A for the process according to scheme-2 or according to its step b) of claim 8. Furthermore, a chlorinating agent of the invention is Cl$_2$, which is inexpensive compared to oxalylchloride, thionylchloride or PCl$_5$, which are disclosed on page 8 of the WO 01/72706 A as possible chlorinating agents. No waste or by products such as CO$_2$, CO, SO$_2$, SO$_3$ or phosphor derivatives are produced in the step, when the chlorine is introduced into the precursor.

The process of the invention allows to carry out reaction (C) and reaction (B) consecutively without isolation of the intermediate compound of formula (IV), the two reaction can be done in the same solvent and even in one pot.

Continuous reaction mode can easily be applied.

The process of the invention provides for bright, white solids in high yields, the solids are obtained as suspensions which show good filtration behaviour.

Compared to WO 01/72706 A, no free acid as intermediate occurs, which has naturally an enhanced solubility in water and therefore complicates its isolation from an organic phase used in the reaction. The process of WO 01/72706 disclosed in examples 1.4 and 1.5 and scheme-1 starts with a free C2-carboxylic acid and a further free C4 carboxylic acid is isolated as intermediate.

EXAMPLES

List of Abbreviations and Raw Materials
Amberlyst 15® DRY CAS 39389-20-3; divinylbenzene-styrenesulfonic acid copolymer, strongly acidic cation exchange resin used as a heterogeneous acid catalysis; suitable for non-aqueous catalysis, and has a concentration of acid sites of at least 4.7 eq/kg. Amberlyst 15® DRY is a product of Rohm and Haas, and was used with the specifications of August 2005.
DBU 1,8-Diazabicyclo[5.4.0]undec-7-ene
DMAP N,N-Dimethyl-4-pyridinamine
TMEDA Tetramethylethylendiamine
eq equivalent(s)

Example 1a

To a solution of a compound of formula (VI) (5.25 g, 62.4 mmol) in dichloromethane (50 mL) of −15° C., Cl$_2$ (4.43 g, 62.4 mmol) was added during 30 min at −15° C. A solution of compound of formula (1) was formed.

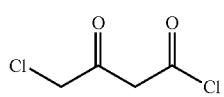
(1)

This solution of compound of formula (1) was then added within 45 min to a mixture consisting of a compound of formula (V) (9 g, 62.4 mmol), NEt$_3$ (12.65 g, 124.9 mmol) and dichloromethane (50 mL) of −15° C. The resulting reaction mixture was stirred for 2 h at 0° C. Amberlyst® 15 DRY (18 g) was added and the reaction mixture was no longer cooled and allowed to warm to room temperature. The Amberlyst® 15 DRY was filtered off and aqueous HCl (1M, 100 mL) was added to the filtrate. The phases were separated, the organic phase was dried over Na$_2$SO$_4$, filtered and concentrated under reduced pressure to provide the compound of formula (2) as a solid (15.1 g, 92%).

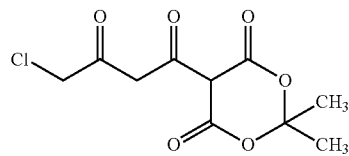
(2)

$^1$H NMR (400 MHz, CDCl$_3$): δ 1.75 (s, 6H), 4.26 (s, 2H), 4.29 (s, 2H), 14.8 (s, 1H)

Example 1b

To a solution of a compound of formula (VI) (17.5 g, 0.21 mol) in dichloromethane (90 mL) at −15° C., Cl$_2$ (14.76 g, 0.21 mol) was added during 120 min. The reaction mixture was stirred at −10° C. for 45 min. A solution of compound formula (1) was formed. To this solution of compound of formula (1) was then added within 60 min a mixture consisting of a compound of formula (V) (30 g, 0.21 mol), NEt$_3$ (42.13 g, 0.42 mol) and dichloromethane (100 mL) of −15° C. The resulting reaction mixture was stirred for 16 h at 0° C. The reaction mixture was acidified with HCl (1M, 100 mL) at room temperature resulting in a dark brown mixture. The two phases could not be observed unambiguously, phase separation was therefore done based on calculated expected volumes of the expected phases. The phases were separated, the organic phase was extracted 3 times and was dried over Na$_2$SO$_4$. The solids were filtered off, filtration was slow. The remaining solvent was removed in vacuo to provide the compound of formula (2) as a dark brown solid (52.2 g, 96%).

Example 1c

To a solution of a compound of formula (VI) (5.25 g, 62.4 mmol) in dichloromethane (50 mL) at −15° C., Cl$_2$ (4.43 g, 62.4 mmol) was added during 35 min. A solution of compound formula (1) was formed. This solution of compound of formula (1) was then added within 60 min to a mixture consisting of a compound of formula (V) (9 g, 62.4 mmol), NEt$_3$ (12.65 g, 124.9 mmol) and dichloromethane (54 mL) at −15° C. The resulting reaction mixture was stirred for 2.5 h at 0° C. Amberlyst® 15 DRY (18 g) was added and stirring was continued for 30 min. The reaction mixture was then allowed to warm to room temperature. The Amberlyst® 15 DRY was filtered off; the reaction mixture was filtered over Celite® and finally concentrated to dryness to yield the compound of formula (2) as a solid (14.2 g, 87%).

Example 1d

To a solution of a compound of formula (VI) (10.5 g, 0.13 mol) in dichloromethane (108 mL) at −20° C., Cl$_2$ (8.86 g, 0.13 mol) was added during 105 min. A solution of compound formula (1) was formed. This solution of compound of formula (1) was then added within 90 min to a mixture consisting of a compound of formula (V) (18 g, 0.13 mol), NEt$_3$ (25.28 g, 0.25 mol) and dichloromethane (110 mL) at −15° C. The resulting reaction mixture was stirred for 2.5 h at −10° C. Amberlyst® 15 DRY (32 g) was added and stirring was continued for 30 min at 0° C. The reaction mixture was then filtered over silica; then acidified with HCl (1M, 150 mL) at 2° C. The phases were separated, the aqueous phase was extracted with dichloromethane (100 mL) and the combined organic phases were dried over Na$_2$SO$_4$, filtered and concentrated under reduced pressure to provide the compound of formula (2) as a solid (28.3 g, 86%).

Example 1e

To a solution of a compound of formula (VI) (7.87 g, 0.09 mol) in dichloromethane (77 mL) at −15° C., Cl$_2$ (6.44 g, 0.09 mol) was added during 60 min. The reaction mixture was stirred at −10° C. for 75 min. A solution of compound formula (1) was formed. To this solution of compound of formula (1) was then added within 60 min a mixture consisting of a compound of formula (V) (10.8 g, 0.07 mol), NEt$_3$ (16.68 g, 0.16 mol) and dichloromethane (80 mL) of −15° C. The resulting reaction mixture was stirred for 16 h at −10° C. The reaction mixture was acidified to pH 1 with gaseous HCl (6 g) at 5° C. resulting in a yellow-brownish reaction mixture. Water (120 mL) was added and the phases were separated, and dried over Na$_2$SO$_4$. The solvent was removed in vacuo to provide the compound of formula (2) as a yellow solid (19.7 g, 80%).

Example 1f

To a solution of a compound of formula (VI) (7.87 g, 0.09 mol) in dichloromethane (77 mL) at −15° C., Cl$_2$ (6.44 g, 0.09 mol) was added during 60 min. The reaction mixture was stirred at −10° C. for 75 min. A solution of compound formula (1) was formed. To this solution of compound of formula (1) was then added within 60 min a mixture consisting of a compound of formula (V) (10.8 g, 0.07 mol), NEt$_3$ (16.68 g, 0.16 mol) and dichloromethane (80 mL.) of −15° C. The resulting reaction mixture was stirred for 16 h at −10° C. The reaction mixture was acidified to pH 1 with conc. H$_2$SO$_4$ (13.3 g) at 5° C. resulting in a yellow brownish mixture. Water (120 mL) was added and the phases were separated, and dried over Na$_2$SO$_4$. The solvent was removed in vacuo to provide the compound of formula (2) as a brown solid (16.3 g, 66%).

Example 1g

To a solution of a compound of formula (VI) (39.4 g, 0.469 mol) in dichloromethane (340 mL) at −15° C., Cl$_2$ (33.3 g, 469 mol) was added during 120 min. The reaction mixture was stirred at −10° C. for 180 min. A solution of compound formula (1) was formed. To this solution of compound of formula (1) was then added within 120 min a mixture consisting of a compound of formula (V) (52 g, 0.361 mol), TMEDA (83.9 g, 0.722 mol) and dichloromethane (340 mL) of −5° C. The resulting reaction mixture was stirred for 4 h at −5° C. The reaction mixture was transferred into aqueous solution of HCl (5% by weight of HCl, based on the total weight of the aqueous solution of HCl, 658 g) at 5° C. resulting in a yellow brownish mixture with a pH below 2. After the phases were separated, the solvent was removed in vacuo to provide the compound of formula (2) as a brown solid with a purity of 80% (101 g, 86% yield).

Example 2a

A mixture of compound of formula (2) (7.5 g, 28.3 mmol), prepared according to example 1, and tert-butanol (75 mL, 0.81 mol) was stirred at reflux for 2.5 h. The resulting reaction mixture was filtered over silica and concentrated under reduced pressure to provide compound of formula (3) (6.4 g, 96%).

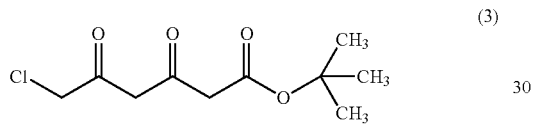

(3)

$^1$H NMR (400 MHz, CDCl$_3$): ratio of an enol form (-ef)/a keto form (-kt)=86:14 (area:area); δ 1.48 (s, 9H-ef), 1.49 (s, 9H-kf), 3.31 (s, 2H-ef), 3.49 (s, 2H-kf), 3.92 (s, 2H-kf), 4.06 (s, 2H-ef), 4.20 (s, 2H-kf), 5.97 (s, 1H-ef)

Example 2b

A mixture of compound of formula (2) (5.2 g, 19.8 mmol), prepared according to example 1, and tert-butanol (52 mL, 0.55 mol) was stirred at reflux for 2.5 h. The resulting reaction mixture was concentrated under reduced pressure to provide compound of formula (3) (4.5 g, 97%).

Example 2c

A mixture of compound of formula (2) (20 g, 76 mmol), prepared according to example 1, tert-butanol (56 g, 0.76 mol) and p-toluene sulfonic acid monohydrate (0.66 g, 4 mmol) was stirred at 50° C. for 3.5 h. The resulting reaction mixture was dissolved in DCM (150 ml) and washed with water (150 ml). The organic phase was mixed with water (150 ml), aqueous NaOH (25% w/w) was added until the pH was 8.0 to 9.0, after phase separation aqueous 0.5 N HCl was added until the pH was 2.5 to 3.5, and the mixture was concentrated under reduced pressure to provide compound of formula (3) (14 g, yield of 63%).

The invention claimed is:

1. A method (PREP) for the preparation of a compound selected from the group consisting of a compound of formula (X), a compound of formula (XI), a compound of formula (XII), Rosuvastatin and Atorvastatin;

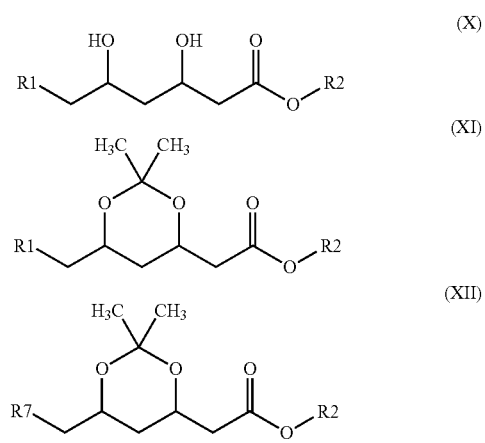

method (PREP) comprises the step (C) and the step (B);
step (B) is done after step (C);
step (C) comprises a reaction (C) of a compound of formula (VI) with a compound (C) to provide a compound of formula (IV);

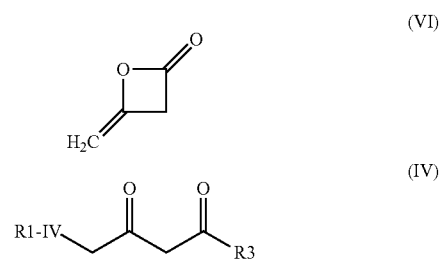

the compound (C) is selected from the group consisting of Cl$_2$, Br$_2$ and ClBr;
step (B) comprises a reaction (B) of the compound of formula (IV), which has been prepared in step (C), with a compound of formula (V) in the presence of a base (B) to provide a compound of formula (II);

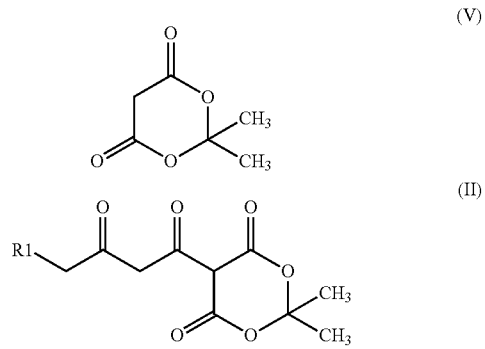

R1 is Cl, Br or CN;
R1-IV and R3 are identical and are Cl or Br;
R2 is a C$_{1-4}$ alkyl;
base (B) is selected from the group consisting of N(R4)(R5)R6, 1,4-diazabicyclo [2.2.2]octane, 1,8-diazabicyclo[5.4.0]undec-7-ene, pyridine, pyridine substituted with 1 or 2 independently selected identical or different C$_{1-2}$ alkyl residues, N,N-dimethyl-4-pyridinamine, morpholine, 4-methylmorpholine, 1-methylpiperidine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, and mixtures thereof;

R4, R5, R6 are identical or different and independently from each other selected from the group consisting of H, C$_{1-15}$ alkyl, C$_{5-6}$ cycloalkyl, (C(R16)R17)$_m$N(R12)R13 and phenyl, with the proviso, that at least one of the residues R4, R5 or R6 is not H;

R7 is O—C(O)CH$_3$, OH or CH$_2$—NH$_2$;

R12 and R13 are identical or different and independently from each other H or C$_{1-15}$ alkyl;

m is 2, 3, 4, 5 or 6;

R16 and R17 are identical or different and independently from each other selected from the group consisting of H, methyl and ethyl;

with the proviso, that if R1 or R7 is CN, then
step (B) comprises additionally a reaction (B-add), the reaction (B-add) is done after the reaction (B), of the reaction product of the reaction (B) with a compound (B);
compound (B) is selected from the group consisting of NaCN, KCN, Si(R9)(R10)(R11)CN, HCN, tetrabutylammonium cyanide, 1-cyano benzotriazole and triselenium dicyanide and mixtures thereof;
R9, R10 and R11 are identical or different and independently from each other selected from the group consisting of C$_{1-4}$ alkyl and phenyl.

2. The method (PREP) according to claim 1, wherein method (PREP) comprises a step (ACID);
step (ACID) is done after step (B);
step (ACID) comprises combining the reaction mixture prepared in step (B) with an acid (B);
acid (B) is selected from the group consisting of polymeric sulfonic acid resin, toluene sulfonic acid, HCl, H$_2$SO$_4$, citric acid, tartaric acid, acetic acid, ammonium chloride, oxalic acid, phosphoric acid and mixtures thereof.

3. The method (PREP) according to claim 2, wherein acid (B) is a polymeric sulfonic acid resin.

4. The method (PREP) according to claim 1, wherein R1-IV and R3 are Cl.

5. The method (PREP) according to claim 1, wherein base (B) is selected from the group consisting of NEt$_3$, tetramethylethylendiamine and N,N-dimethyl-4-pyridinamine and mixtures thereof.

6. The method (PREP) according to claim 1, wherein base (B) is selected from the group consisting of pyridine, pyridine substituted with 1 or 2 independently selected identical or different C$_{1-2}$ alkyl residues, morpholine, 4-methylmorpholine, 1-methylpiperidine, imidazol, benzimidazol, 2-methylimidazole, 4-methylimidazole, 2-ethylimidazole, 2-ethyl-4-methylimidazole, 2-isopropylimidazole, 2-phenylimidazole, 4-phenylimidazole, picoline, and mixtures thereof.

7. The method (PREP) according to claim 1, wherein R4, R5, R6 are identical or different and independently from each other selected from the group consisting of cyclohexyl, phenyl, methyl, ethyl, n-propyl, iso-propyl, n-butyl, iso-butyl, sec-butyl, tert-butyl and (CH$_2$)$_m$N(R12)R13;
R12 and R13 are identical or different and independently from each other selected from the group consisting of H, methyl, ethyl, n-propyl, iso-propyl, n-butyl, iso-butyl, sec-butyl and tert-butyl;
m is 2, 3 or 4.

8. The method (PREP) according to claim 1, wherein R9, R10 and R11 are identical and are selected from the group consisting of C$_{1-4}$ alkyl.

9. The method (PREP) according to claim 1, wherein compound (B) is NaCN or KCN.

10. The method (PREP) according to claim 1, wherein reaction (B) is done in a solvent (B);
solvent (B) is selected from the group consisting of hexanes, heptanes, dichloromethane, dichloroethane, chloroform, carbon tetrachloride, toluene, xylene, mesitylene, dioxane, methyl tert-butyl ether and mixtures thereof.

11. The method (PREP) according to claim 1, wherein compound (C) is Cl$_2$ or Br$_2$.

12. The method (PREP) according to claim 1, wherein reaction (C) is done in a solvent (C),
solvent (C) is selected from the group consisting of hexane, heptane, dichloromethane, dichloroethane, chloroform, carbon tetrachloride, toluene, xylene, mesitylene, dioxane, methyl tert-butyl ether and mixtures thereof.

13. The method (PREP) according to claim 1, wherein compound (C) is Cl$_2$,
R1-IV and R3 are Cl and
R1 is Cl or CN.

14. The method (PREP) according to claim 1, wherein method (B) comprises further a step (A);
step (A) is done after step (B);
step (A) comprises a reaction (A) of compound of formula (II), which has been prepared in step (B), with a compound of formula (III) to provide compound of formula (I);

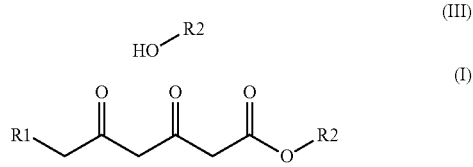

R2 is C$_{1-4}$ alkyl.

15. The method (PREP) according to claim 14, wherein R1 is Cl or CN.

16. The method (PREP) according to claim 14, wherein R2 is ethyl or tert-butyl.

17. The method (PREP) according to claim 14, wherein method (B) comprises step (ACID);
step (ACID) is done before step (A);
step (ACID) is done after step (B);
step (ACID) comprises combining the reaction mixture prepared in step (B) with an acid (B);
acid (B) is selected from the group consisting of polymeric sulfonic acid resin, toluene sulfonic acid, HCl, H$_2$SO$_4$, citric acid, tartaric acid, acetic acid, ammonium chloride, oxalic acid, phosphoric acid and mixtures thereof.

18. The method (PREP) according to claim 17, wherein acid (B) is a polymeric sulfonic acid resin.

19. The method (PREP) according to claim 1 for the preparation of a compound selected from the group consisting of a compound of formula (X), a compound of formula (XI), a compound of formula (XII), and Rosuvastatin.

20. The method (PREP) according to claim 1 for the preparation of a compound selected from the group consisting of a compound of formula (X), a compound of formula (XI), and a compound of formula (XII).

* * * * *